United States Patent [19]

Paap et al.

[11] 4,352,288
[45] Oct. 5, 1982

[54] MEASUREMENT OF SALT CONTENT IN PETROLEUM FLOW LINES

[75] Inventors: Hans J. Paap, Houston; Richard A. Meador, Spring; Dan M. Arnold, Houston, all of Tex.

[73] Assignee: Texaco Inc., White Plains, N.Y.

[21] Appl. No.: 171,766

[22] Filed: Jul. 24, 1980

[51] Int. Cl.³ ............................................ G01N 33/26
[52] U.S. Cl. .................................... 73/61 R; 378/47
[58] Field of Search ................ 73/61 R, 61.1 R, 53, 73/32 R; 250/272, 273; 324/65 R

[56] References Cited

U.S. PATENT DOCUMENTS 4,266,425  5/1981  Allport ............................... 73/61 R Primary Examiner—Kyle L. Howell
Assistant Examiner—Joseph W. Roskos
Attorney, Agent, or Firm—Carl G. Ries; Robert A. Kulason; Jack H. Park

[57] ABSTRACT

The salt content of a fluid in a pipeline or container in petroleum producing or refining operations is determined by obtaining a measure of water cut of an oil-water-free gas fluid mixture. The conductivity of the fluid is measured by radio frequency (RF) induction techniques, while the density of the fluid is measured and related to the liquid phase fraction of the fluid using gamma radiation techniques. The conductivity and liquid phase fraction are then used to determine salt content of the liquid phase.

17 Claims, 8 Drawing Figures

MEASUREMENT OF SALT CONTENT IN PETROLEUM FLOW LINES

BACKGROUND OF INVENTION

1. Field of Invention

The present invention relates to measuring salt content of fluids in petroleum operations.

2. Description of Prior Art

U.S. patent application Ser. Nos. 872,981 filed Jan. 27, 1978 now U.S. Pat. No. 4,209,695 (Texaco D#74,465C1); and 920,568, filed June 28, 1978 now U.S. Pat. No. 4,200,789 (Texaco Docket No. D#76,534), of common ownership with the present invention, deals with a thermal neutron capture technique of measuring the presence and concentration of salt water in fluid in a refinery pipeline or other petroleum producing or refining operation. For accurate results where there was free gas in the fluid stream, it was required that the free gas be distributed homogenously within the liquid phase. This was often the case at some points in petroleum production operations such as at the output of a gas-oil separator or at a loading dock manifold. However, it would also be desirable to monitor salt content in well flow lines where free gas is not homogenously distributed.

U.S. patent application Ser. Nos. 106,585, filed Dec. 26, 1979; and 106,584, filed Dec. 26, 1979, also of common ownership with the present invention, utilized a gamma ray energy emitter and a microwave energy transmitter to obtain a measure of the water cut of an oil-water-free gas mixture. From the water cut and a knowledge of water salinity, the amount of salt in pounds per thousand barrels (PTB) can be obtained.

SUMMARY OF INVENTION

Briefly, the present invention relates to analysis of fluid flowing in a conduit to determine the salt content of the fluid. The conductivity of the fluid is measured, preferably by subjecting the fluid to radio frequency energy from an inductive coil and measuring the changes in inductance of the coil due to changes in conductivity of the liquid.

The liquid is also subjected to gamma radiation and a measure of the density of the fluid is obtained from the gamma radiation transmitted through the fluid. Based on the density of the fluid, the liquid phase fraction of the fluid is measured. With the liquid phase fraction and conductivity of the fluid determined, the concentration of salt in the liquid phase of the fluid is then determined.

DESCRIPTION OF THE PREFERRED EMBODIMENT

Figure 2:
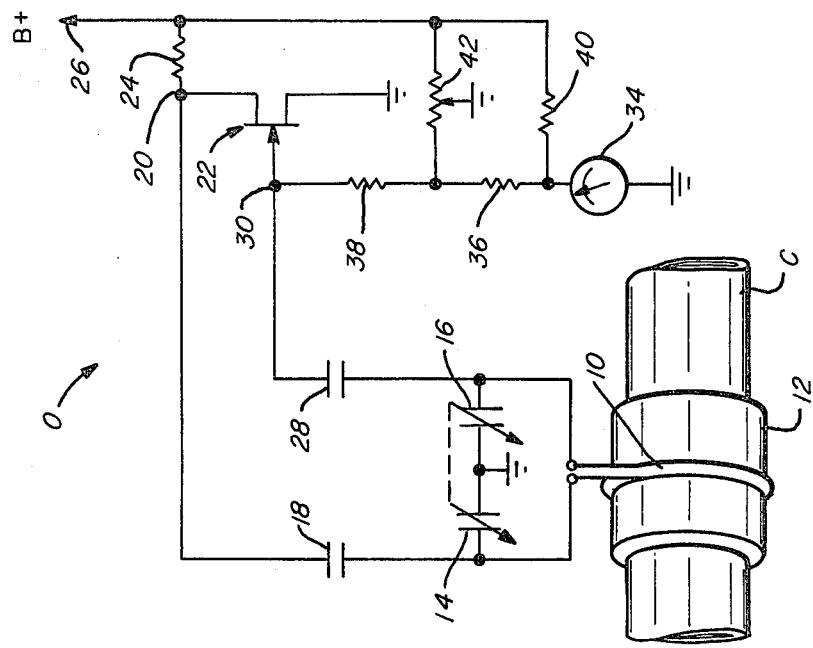
FIG. 2 is a schematic electrical circuit diagram of a portion of FIG. 1.

In the drawings, the letter A designates generally an apparatus for analysis of a fluid flowing in a conduit or pipe P to determine the salt content of the fluid. The fluid contains a liquid phase of petroleum product and water and may have gas non-homogenously mixed therein. The conduit P is formed from a non-conductive material and may be a section, for example, of fiberglass pipe connected as part of a petroleum refining conduit containing either feed stock or refined product, or as part of a well head conduit at an oil well or as part of a conduit at a loading dock containing crude oil.

The apparatus A includes an oscillator circuit O which subjects the fluid in the conduit to radio frequency energy to measure the conductivity of the fluid. The apparatus A further includes a gamma radiation/detection circuit G which radiates the fluid in the conduit P with gamma radiation and measures the gamma radiation transmitted through the fluid to obtain a measure of the density of the fluid so that the liquid phase fraction of the fluid may be obtained. Based on the measure of the conductivity of the fluid obtained in the oscillator circuit O and the liquid phase fraction of the fluid obtained from the measurement of density in the circuit G, the concentration of salt in the liquid phase of the fluid in the conduit P is obtained in accordance with the present invention, so long as the conductive phase (water) is the continuous phase. The present invention is not adapted for determining salt content of water in oil emulsions.

Considering now the oscillator circuit O (FIGS. 1 and 2) more in detail, an inductive coil 10 in the form of a number of turns dependent upon the frequency of oscillation is wrapped on a mounting sleeve 12 about the perimeter of the conduit P at a suitable location. The coil 10, when energized, subjects the fluid in the conduit P to radio frequency energy. Electrically connected in a parallel circuit arrangement with the coil 10 are variable capacitors 14 and 16 which are simultaneously adjustable, as indicated in the drawings. The coil 10 and capacitor 14 are electrically connected through a capacitor 18 to a source terminal 20 of a field effect transistor (FET) 22 which receives operating power through a resistor 24 from a suitable power supply connected to a terminal 26. The coil 10 and capacitor 16 are electrically connected through a capacitor 28 to a gate terminal 30 of the field effect transistor 22.

An ammeter 34 or other suitable current measuring device is electrically connected to the gate terminal 30 through resistors 36 and 38 so that the amount of current flowing into the gate terminal 30 of the field effect transistor 22 may be measured. The meter 34 is electrically connected through a resistor 40 to the power supply terminal 26. A sensitivity adjustment resistor 42 is electrically connected between the terminal 26 and the common connection between the resistors 36 and 38 so that the sensitivity of the oscillator circuit O may be adjusted as desired.

As can be seen from the drawings, the oscillator O is configured as a parallel resonant LC or Colpitts oscillator which subjects the fluid in the conduit P to radio frequency energy from the coil 10. The inner volume of the coil 10 is filled with the conduit P and the fluid therein. As the salinity of the fluid in the conduit P varies, the conductivity of the material within the inner volume of the coil 10 varies. Due to the induction by the primary magnetic field of the coil 10, electrical currents are generated within any conductive material in the fluid within the coil 10. The current density is determined by the strength of the primary magnetic field and the conductivity of the fluid within the conduit P within the coil 10. The currents in the coil 10 generate a secondary magnetic field which induces a secondary electrical current in the coil 10 opposing the primary current flowing through the coil 10. The reduction of the primary current by the secondary electrical current can be considered as analogous to introduction of a resistance in series with the coil 10. Since the coil 10 is the inductive portion of the parallel LC resonant oscillator circuit O formed with the capacitors 14 and 16, the effect of the reduction of primary current by the secondary current is a lowering of the Q of the resonant oscillator circuit O based upon the conductivity of the fluid within the coil 10.

Variations in the Q of the oscillator circuit O are indicated and measured as changes in the gate current of the field effect transistor 22 with the meter 34. Changes in the grid current of the field effect transistor 22 indicate changes in the conductivity of the fluid within the conduit P in the vicinity of the coil 10. It should also be understood that other semiconductors or a triode or higher terminal vacuum tube may be used in place of the field effect transistor 22. Where a vacuum tube is used, capacitor 30 is electrically connected to the grid terminal thereof.

When the gas/liquid ratio of the fluid in the conduit P is determined in the manner to be set forth below, the salt content in parts per million (ppm) or in parts per thousand barrels (PTB) can be determined.

The gamma radiation/detection circuit G is in the form of a gamma ray densitometer which incluides a ten microcurie $Cs^{137}$ gamma ray source 44 mounted within a lead collimator 46 which irradiates the fluid in the conduit P with gamma radiation. A $2''\times2''$ NaI(Tl) crystal detector 48 is mounted opposite the source 44 with respect to the conduit P. The detector 48 produces scintillations or discrete flashes of light when gamma rays are received. A photomultiplier tube 50 is mounted adjacent the crystal 48 and generates voltage pulses in response to each scintillation from the crystal 48. The photomultiplier tube 50 receives operating power from a high voltage power supply 51.

The voltage pulses formed in the photomultiplier tube 50 are proportional in intensity to the intensity of each flash or scintillation formed in the crystal 48, which, in turn, is proportional to the energy of the received gamma radiation. A conventional preamplifier circuit 52 receiving operating power from a power supply 54 amplifies the pulses from the photomultiplier tube 50 and furnishes the amplified pulses to a further amplifier stage 54.

The output pulses from amplifier 56 are furnished to a gain stabilizer circuit 58 which is calibrated to respond to the energy level of a selected reference peak in the gamma ray energy spectrum, such as the 0.66 MeV energy peak of $Cs^{137}$ of the element cesium. The gain stabilizer circuit 58 is an automatic gain control circuit which responds to the energy level of pulses at the calibrated peak level and adjusts the gain of all energy level pulses from the photomultiplier tube 50 to compensate for gain shifts or variations in the tube T and other circuitry of the circuit G due to power supply voltage fluctuations and/or temperature effects and the like.

Figure 1:
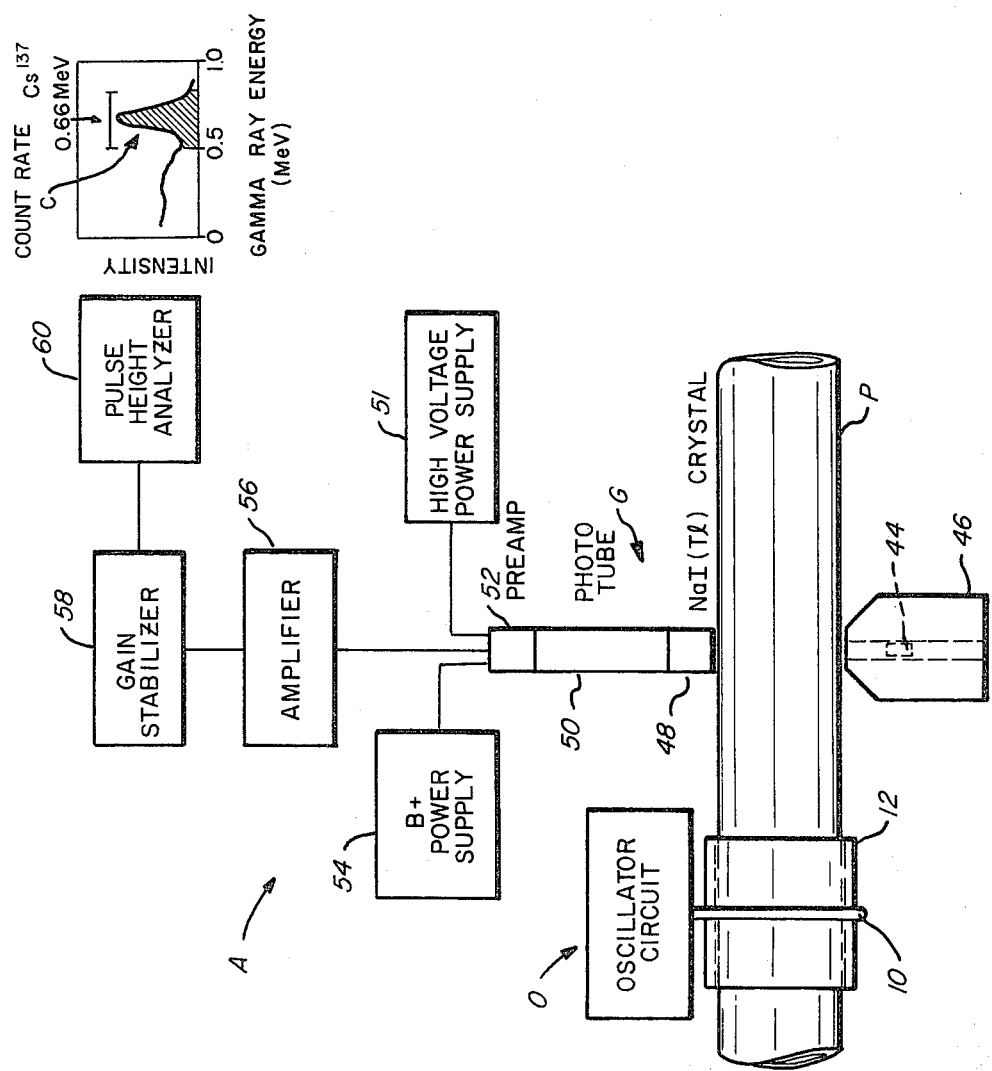
FIG. 1 is a schematic diagram of an apparatus of the present invention.

Output pulses from the gain stabilizer circuit 58 are furnished to a pulse height or multi-channel analyzer 60 which sorts and accumulates a running total of the incoming pulses into a plurality of storage locations or channels based on the height of the incoming pulses. As has been previiously set forth, the height of the incoming pulses is directly related to the energy of the gamma rays received in the crystal 48 causing such pulses. The pulse height analyzer 60 in the preferred embodiment is set to count incoming gamma radiation pulses in the range from 0.5 to 1.0 MeV, as depicted in FIG. 1. It should be understood, however, that other energy ranges may be utilized as well, depending upon the source of gamma radiation in the source 44.

The pulse height analyzer 60 accumulates a count C from which the fluid density $\rho$ may be determined in accordance with the following equation:

$$\rho = K1n(C_o/C) \qquad (1)$$

where C is the count rate of primary 0.66 MeV radiation transmitted through the fluid in the conduit P, and K and $C_0$ are calibration constants.

The calibration constants K and $C_0$ may be determined by measuring count rates with the conduit V filled with water ($\rho \cong 1.0$ gm/cm$^3$) and air ($\rho \cong 0.0$ gm/cm$^3$). Count rate measurements obtained for these known fluid densities yield two versions of Equation (1) above which may then be solved simultaneously for K and $C_0$. For a gamma radiation circuit G of the type set forth above, with a three inch diameter conduit P, values as set forth below were obtained:

$C_0 = 375$ counts/second $K = 1.96$ gm/cm$^3$

Figure 5B:
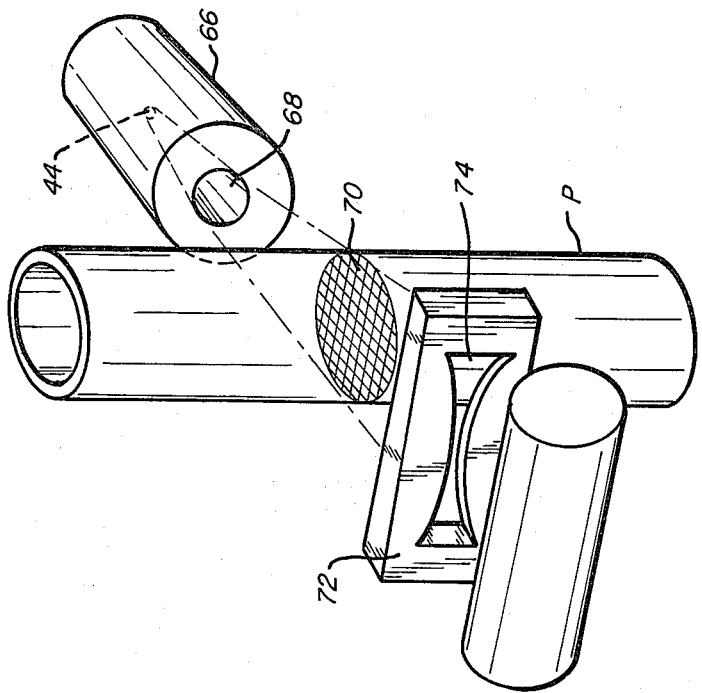
FIGS. 5A and 5B are schematic diagrams of alternative means for collimating gamma radiation into a fluid in a conduit according to the present invention.
Figure 5A:
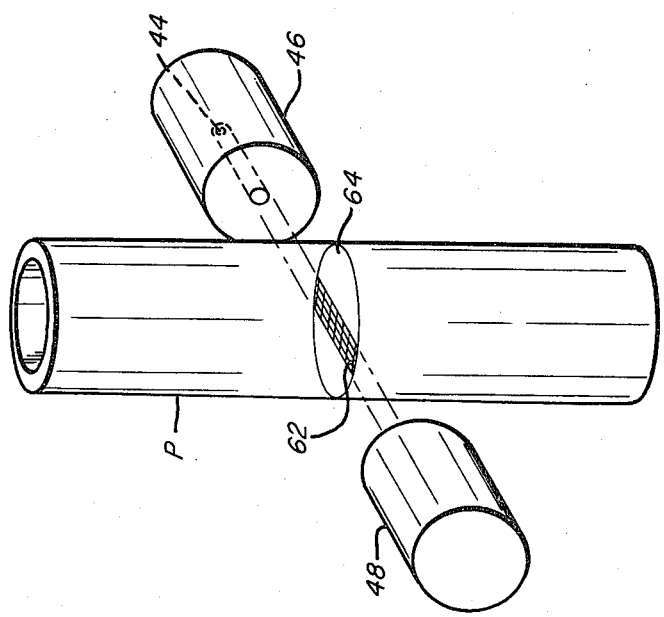

As can be seen in FIG. 5A, only a fractional portion 62 of a cross-sectional area 64 within the conduit P is subjected to radiation from the source 44. However, so long as the fluid mixture in the conduit P is nearly homogenous, no error is introduced. In situations where multiphase flows are present in the conduit P which might not be homogenous, an alternative collimating arrangement is provided (FIG. 5B).

In the alternative arrangement, a lead collimator 66 has the source 44 mounted therein at an inner end of a conical opening or recess 68. Gamma radiation from the source 44 is thus collimated to pass through an entire cross-sectional area 70 within the pipe P. After the gamma radiation has passed through the conduit P, a further collimator 72 focuses the gamma radiation incident through a slot 74 onto the detector 48, which is rotated 90° in position from its location in FIG. 5A.

The measured density $\rho$ for a multiphase fluid in conduit P can be expressed as:

$$\rho = V_G \rho_G + V_o \rho_o + V_W \rho_W \qquad (2)$$

where $V_G$, $V_o$, $V_W$ and $\rho_G$, $\rho_o$, $\rho_W$ are the volume fractions and densities of the gas, oil, and water phases of the fluid, respectively. $V_L$, the liquid phase fraction of the fluid, is given by the equation:

$$V_L = V_o + V_W \qquad (3)$$

Figure 7:
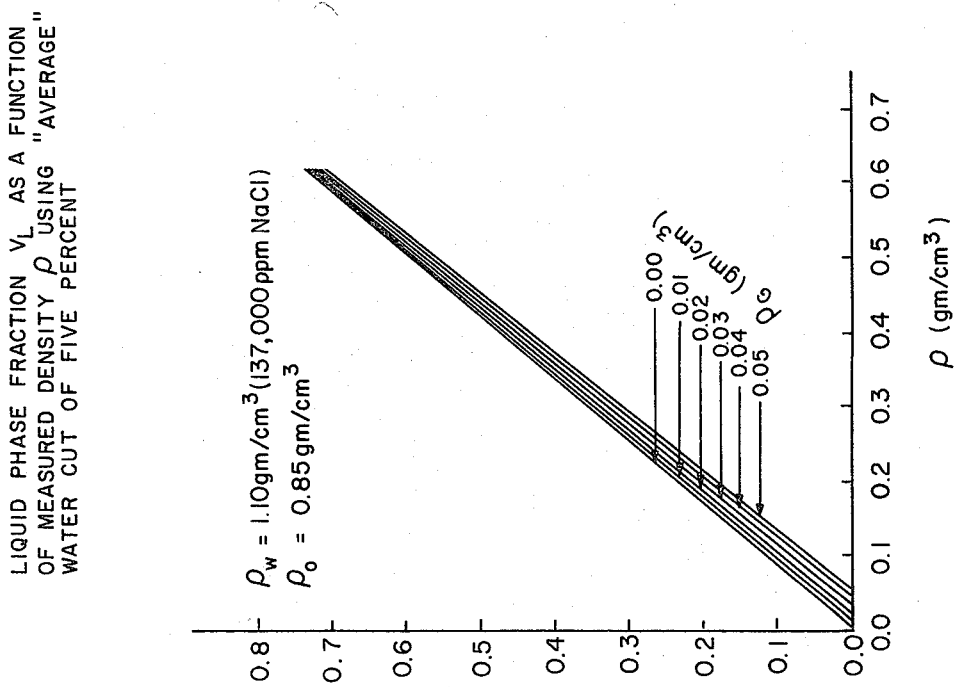
FIGS. 6 and 7 are plots of liquid phase fraction as functions of measured liquid density in a fluid.
Figure 6:
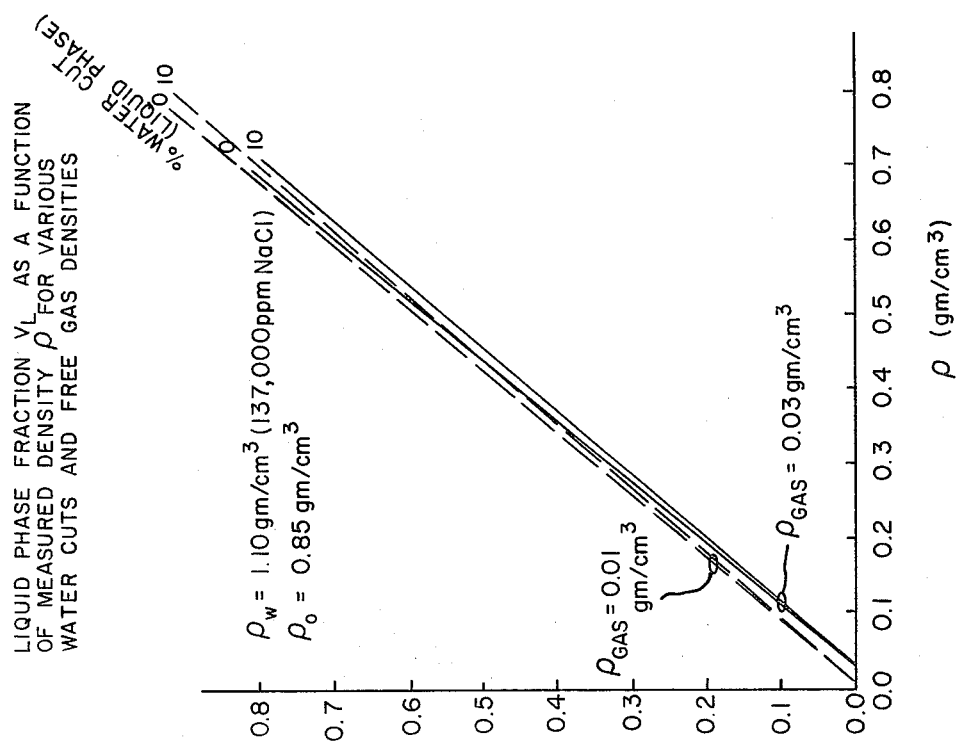

FIG. 6 shows a plot of $V_L$ as a functions of $\rho$ for various free gas densities and percent water cuts obtained by percolating measured amounts of air bubbles into water- /oil mixture in the pipe P upstream of the apparatus A. Density values for $\rho_o$ and $\rho_W$ were set at 0.85 gm/cm$^3$ and 1.10 gm/cm$^3$, respectively. It can be seen that for a given free gas density, $\rho$ is affected very little when the water cut is varied between 0 and 10%. It should also be noted that variations in $\rho_W$ from 1.00 gm/cm$^3$ (fresh water) to 1.17 gm/cm$^3$ (230,000 ppm NaCl) have little affect on $V_L$ as a function of $\rho$. It has been found according to the present invention, therefore, that it is not necessary to know the salinity of the produced water to obtain $V_L$ from $\rho$. In addition, water cuts of 10% or less have little influence on $V_L$ as a function of $\rho$ and need not be known. $\rho_G$ does, however, appreciably affect $V_L$ especially for fluids with high gas/liquid ratios. $\rho_G$ can usually be computed quite accurately from pressure, volume and temperature data readily obtainable along the conduit P. Using this calculated value of $\rho_G$ and the appropriate "average" water cut (5%) line shown in FIG. 7, it is possible to relate the measured quantity $\rho$ to the liquid phase fraction $V_L$.

Figure 4:
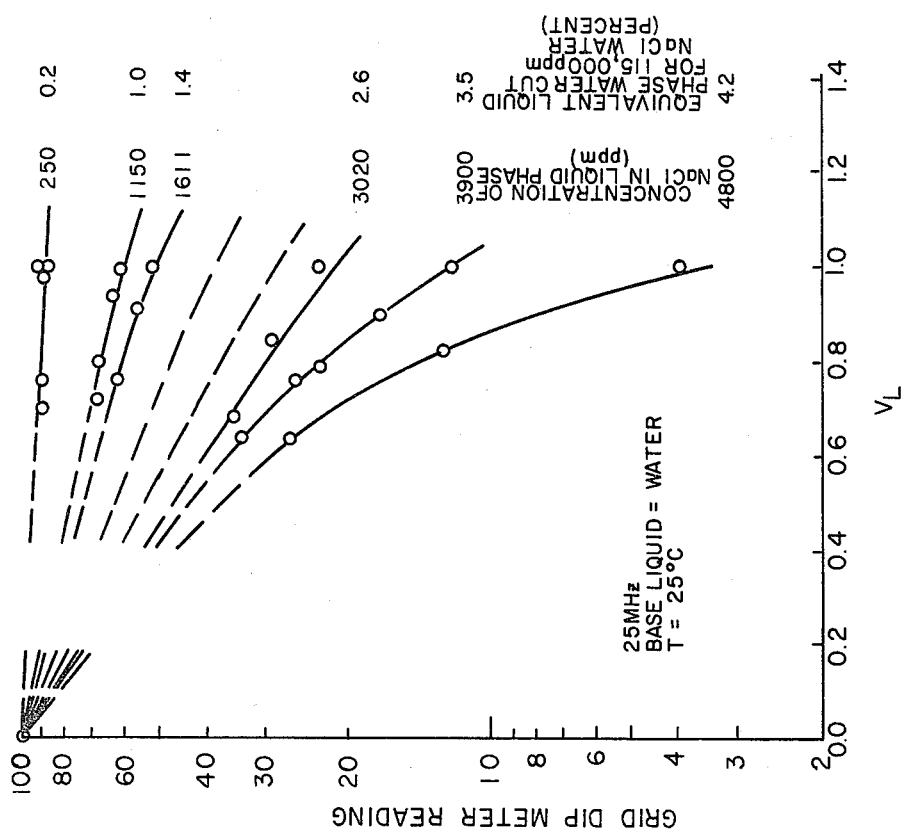
FIGS. 3 and 4 are plots of current readings obtained in the apparatus of FIG. 1 as a function of liquid phase fraction for various concentration of salinity in a fluid.
Figure 3:
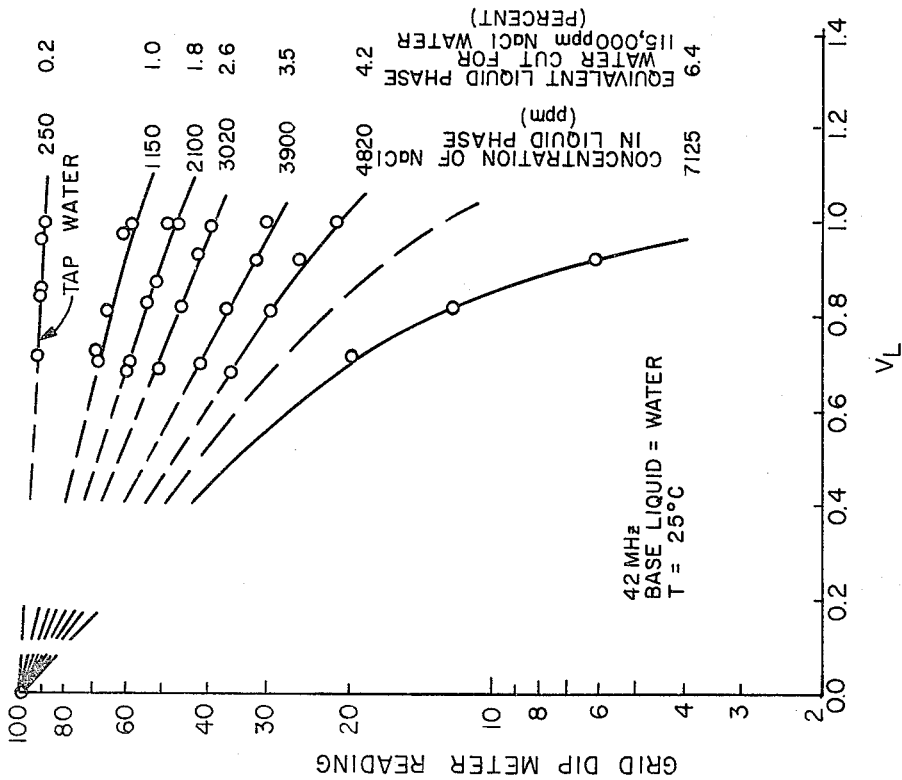

Conductivity measurements as a function of liquid phase fraction $V_L$ are shown in FIG. 3 for water with varying NaCl concentrations obtained as measurements on meter 34 in the apparatus of FIG. 1. These concentrations are also listed as equivalent liquid phase water cut for 115,000 ppm NaCl water. The frequency of oscillator O was 42 MHz for which a base reading for air on meter 34 of one hundred was set by resistor 42. No data points were measured for $0.00 < V_L 21\ 0.65$ due to limited air pressure in the test apparatus. Smooth curves have, however, been drawn through the data points obtained and extrapolated to the measured air point ($V_L=0$). FIG. 4 shows a similar set of measurements at an oscillator frequency of 25 MH$_z$.

The foregoing disclosure and description of the invention are illustrative and explanatory thereof, and various changes in the size, shape and materials, as well as in the details of the illustrated construction may be made without departing from the spirit of the invention.

We claim:

1. A method for analysis of a fluid flowing in a conduit to determine the salt content of the fluid comprising the steps of:
(a) measuring the conductivity of the fluid;
(b) measuring the density of the fluid;
(c) obtaining a measure of the liquid phase fraction of the fluid based on the density of the fluid; and
(d) obtaining from the conductivity and the liquid phase fraction the concentration of salt in the liquid phase of the fluid.

2. The method of claim 1, wherein said step of measuring the density comprises the steps of:
(a) radiating the fluid with gamma radiation;
(b) obtaining a measure of the gamma radiation transmitted through the fluid; and
(c) obtaining a measure of the density of the fluid from the gamma radiation counted.

3. The method of claim 2, wherein said step of radiating includes the step of:
collimating the gamma radiation to pass through only a portion of cross-sectional area of the fluid in the conduit.

4. The method of claim 2, wherein said step of radiating includes the step of:
collimating the gamma radiation to pass through the entire cross-sectional area of the fluid in the conduit.

5. The method of claim 2, wherein said step of radiating comprises the step of:
radiating the fluid with Cs$^{137}$ gamma radiation.

6. The method of claim 5, wherein said step of obtaining a measure of the gamma radiation comprises the step of:
counting gamma rays in the range of from 0.5 MeV to 1.0 MeV.

7. The method of claim 1, wherein said step of measuring the conductivity of the fluid comprises the steps of:
(a) subjecting the fluid to radio frequency energy from an inductive coil;
(b) measuring variations in the inductance of the coil; and
(c) obtaining from the variations in inductance of the coil a measure of the conductivity of the fluid.

8. The method of claim 7, wherein the coil is connected as a part of an oscillator circuit, and wherein said step of measuring variations in the inductance comprises the step of:
measuring current flowing in the oscillator circuit.

9. An apparatus for analysis of a fluid flowing in a conduit to determine the salt content of the fluid, comprising:
(a) means for radiating the fluid with gamma radiation;
(b) means for obtaining a measure of the gamma radiation transmitted through the fluid for obtaining a measure of the density of the fluid;
(c) inductive coil means for subjecting the fluid to radio frequency;
(d) means for measuring variations in the inductance of said inductive coil means for obtaining a measure of the conductivity of the fluid so that the salt content of the fluid may be determined from the measures of density and conductivity obtained.

10. The apparatus of claim 9, wherein said means for radiating comprises:
means for collimating the gamma radiation to pass through only a portion of cross-sectional area of the fluid in the conduit.

11. The apparatus of claim 9, wherein said means for radiating comprises:
means for collimating the gamma radiation to pass through the entire cross-sectional area of the fluid in the conduit.

12. The apparatus of claim 9, wherein said means for radiation comprises:
a Cs$^{137}$ gamma radiation source.

13. The apparatus of claim 9, wherein said means for obtaining a measure of gamma radiation comprises:
(a) detector means for emitting light flashes on receipt of gamma radiation;
(b) photomultiplier means for forming a voltage pulse proportional in height to the intensity of light flashes from said detector means; and
(c) pulse height analyzer means for counting in categories according to height the number of pulses from said photomultiplier means.

14. The apparatus of claim 9, wherein said inductive coil means is electrically connected as part of an oscillator circuit.

15. The apparatus of claim 13, wherein said means for measuring variations in inductance comprises:
means for measuring current in said oscillator circuit.

16. The apparatus of claim 14, wherein said oscillator circuit is a vacuum-tube driven Colpitts oscillator and said means for measuring current comprises:
means for measuring grid current in said vacuum tube.

17. The apparatus of claim 14, wherein said oscillator circuit is a field effect transistor driven Colpitts oscillator and said means for measuring current comprises:
means for measuring gate current in said field effect transistor.

* * * * *